(12) United States Patent
Kudsk

(10) Patent No.: US 6,271,202 B1
(45) Date of Patent: Aug. 7, 2001

(54) REDUCTION OF IMPAIRMENT OF RESPIRATORY TRACT MUCOSAL IMMUNITY

(75) Inventor: Kenneth A. Kudsk, Memphis, TN (US)

(73) Assignee: University of Tennessee Research Corporation, Knoxville, TN (US)

( * ) Notice: Subject to any disclaimer, the term of this patent is extended or adjusted under 35 U.S.C. 154(b) by 0 days.

(21) Appl. No.: 09/067,032

(22) Filed: Apr. 28, 1998

Related U.S. Application Data

(63) Continuation-in-part of application No. 08/842,877, filed on Apr. 17, 1997, now abandoned.
(60) Provisional application No. 60/029,689, filed on Oct. 31, 1996, and provisional application No. 60/015,835, filed on Apr. 19, 1996.

(51) Int. Cl.[7] .............................. A61K 38/00; C07K 5/00; C07K 7/00

(52) U.S. Cl. .............................. 514/12; 514/13; 514/14; 514/15; 514/16; 514/17; 530/300; 530/308; 530/328; 530/329

(58) Field of Search .................... 530/300, 308, 530/329, 328; 514/12, 13, 14, 15, 16, 17

(56) References Cited

U.S. PATENT DOCUMENTS 5,397,803   3/1995   Smith et al. .................... 514/563

OTHER PUBLICATIONS

Janu et al., Archives of Surgery, vol. 132, No. 1, 1997, pp. 89–93.*
Baraniuk et al., "Bombesin Stimulates Human Nasal Mucous and Serous Cell Secretion In Vivo," *American Journal Of Physiology*, vol. 262, pp. L48–L52 (1992).
Baraniuk et al., "Gastrin Releasing Peptide (GRP) Binding Sites in Human Bronchi," *Neuropeptides*, vol. 21, pp. 81–84 (1992).
Chu et al., "Bombesin Improves Survival from Methotrexate–Induced Enterocolitis," *Annals of Surgery*, vol. 220, No. 4, pp. 570–577 (1994).
Debas et al., "Neuroendocrine Design of the Gut," *The American Journal Of Surgery*, vol. 161, pp. 243–249 (1991).
Rio et al., "Bombesin, Gastrin–Releasing Peptide, and Neuromedin C Modulate Murine Lymphocyte Proliferation Through Adherent Accessory Cells and Activate Protein Kinase C," *Peptides*, vol. 15, No. 1, pp. 15–22 (1994).
Evers et al., "Characterization of Functional Neurotensin Receptors on Human Lymphocytes," *Surgery*, vol. 116, pp. 134–140 (1994).

(List continued on next page.)

*Primary Examiner*—Avis M. Davenport
(74) *Attorney, Agent, or Firm*—Morgan, Lewis & Bockius LLP

(57) ABSTRACT

The present invention describes methods for reducing the impairment respiratory tract mucosal immunity associated with a lack of enteral feeding or a lack of immunological stimulation of the gastrointestinal tract comprising administering a therapeutically effective amount of a neuropeptide. Also described are methods for reducing the rate of infection of the respiratory tract by pathogenic microorganisms associated with a lack of enteral feeding or a lack of immunological stimulation of the gastrointestinal tract comprising administering a therapeutically effective amount of a neuropeptide. In addition, a method of reducing the atrophy or dysfunction of the GALT comprising administering a therapeutically effective amount of a neuropeptide is described. The specification further describes compositions for reducing or preventing the impairment of intestinal or respiratory tract mucosal immunity comprising a neuropeptide and a pharmaceutically acceptable carrier.

18 Claims, 4 Drawing Sheets

(1 of 4 Drawing Sheet(s) Filed in Color)

OTHER PUBLICATIONS

Geoghegan et al., "Clinical Uses of Gut Peptides," *Annals Of Surgery*, vol. 225, No. 2, pp. 145–154 (1997).

Haskel et al., "Elemental Diet–Induced Bacterial Translocation Can Be Hormonally Modulated," *Annals of Surgery*, vol. 217, No. 6, pp. 634–643 (1993).

Haskel et al., "The Modulatory Role Of Gut Hormones In Elemental Diet and Intravenous Total Parenteral Nutrition-Induced Bacterial Translocation In Rats," *Journal of Parenteral And Enteral Nutrition*, vol. 18, No. 2, pp. 159–166 (1994).

Haskel et al., "Bombesin Protects Against Bacterial Translocation Induced by Three Commercially Available Liquid Enteral Diets: A Prospective, Randomized, Multigroup Trial," *Critical Care Medicine*, vol. 22, No. 1, pp. 108–113 (1994).

Hauser–Kronberger et al., "Autonomic and Peptidergic Innervation of Human Nasal Mucosa," *Acta otolaryngol (Stockh)*, vol. 113, pp. 387–393 (1993).

Jin et al., "Bombesin: An Activator Of Specific Aeromonas Antibody Secretion In Rat Intestine," *Digestive Diseases And Sciences*, vol. 34, No. 11, pp. 1708–1712 (1989).

Lieverse et al., "Significant Satiety Effect Of Bombesin In Lean But Not In Obese Subjects," *International Journal Of Obesity*, vol. 18, pp. 579–583 (1994).

Sean J. Mulvihill, "Gut Hormones," *Annals Of Surgery*, vol. 225, No. 2, pp. 143–144 (1997).

Muurahainen et al., "Intravenous Infusion of Bombesin Reduces Food Intake In Humans," *The American Journal Of Physiology*, vol. 264, pp. R350–R354 (1993).

C. A. Ottaway, "Neuroimmunomodulation in the Intestinal Mucosa," *Gastroenterology Clinics Of North America*, vol. 20, No. 3, pp. 511–529 (1991).

Pascual et al., "Functional Aspects of the Peptidergic Circuit in Mucosal Immunity," *Handbook Of Mucosal Immunology*, pp. 203–216 (1994).

Spindel et al., "Bombesin–Like Peptides: Of Ligands and Receptors," *Recent Progress In Hormone Research*, vol. 48, pp. 365–391 (1993).

Van Tol et al., "Intravenous Administration of Bombesin in Man Stimulates Natural Killer Cell Activity Against Tumor Cells," *Neuropeptides*, vol. 18, pp. 15–21 (1991).

Abraham et al., "Intranasal Immunization with Bacterial Polysaccharide Containing Liposomes Enhances Antigen–Specific Pulmonary Secretory Antibody Response," *Vaccine*, vol. 10, pp. 461–468 (1992).

Brandtzaeg, *Handbook of Mucosal Immunology*, ed. Ogra et al., Academic Press, San Diego, Chap. 21, pp. 251–262, (1994).

Cebra et al., *Handbook of Mucosal Immunology*, ed. Ogra et al., Academic Press, San Diego, Chap. 13, pp. 151–158 (1994).

Cerra, *Perspect. Crit. Care*, ed. Cerra, Quality Medical Publishing, Inc., St. Louis, vol. 1, pp. 1–30 (1988).

Kilian et al., *Handbook of Mucosal Immunology*, ed. Ogra et al., Academic Press, San Diego, Chap. 11, pp. 127–137 (1994).

Kiyono et al., *Handbook of Mucosal Immunology*, ed. Ogra et al., Academic Press, San Diego, Chap. 22, pp. 263–274 (1994).

Lebman et al., *Handbook of Mucosal Immunology*, ed. Ogra et al., Academic Press, San Diego, Chap. 20, pp. 243–50 (1994).

McGhee et al., "The Mucosal Immune System: from Fundamental Concepts to Vaccine Development," *Vaccine*, vol. 10, pp. 75–88 (1992).

Mestecky et al., *Handbook of Mucosal Immunology*, ed. Ogra et al., Academic Press, San Diego, Chap. 31, pp. 357–372 (1994).

Phillips–Quagliata et al., *Handbook of Mucosal Immunology*, ed. Ogra et al., Academic Press, San Diego, Chap. 19, pp. 225–239 (1994).

Svanborg, *Handbook of Mucosal Immunology*, ed. Ogra et al., Academic Press, San Diego, Chap. 6, pp. 71–78 (1994).

Tomasi, *Handbook of Mucosal Immunology*, ed. Ogra et al., Academic Press, San Diego, Chap. 1, pp. 3–8 (1994).

Alverdy et al., "The Effect of Glutamine–Enriched TPN on Gut Immune Cellularity," *J. Surg. Res.*, vol. 52, pp. 34–38 (1992).

Alverdy et al., "Total Parenteral Nutrition Promotes Bacterial Translocation from the Gut," *Surgery*, vol. 104, pp. 185–190 (1988).

Baker et al., "Epidemiology of Trauma Deaths," *Am. J. Surg.*, vol. 140, pp. 144–150 (1980).

Bone et al., "Sepsis Syndrome: a Valid Clinical Entity," *Crit. Care Med.* vol. 17, pp. 389–393 (1989).

Bone et al., "A Controlled Clinical Trial of High–Dose Methylprednisolone in the Treatment of Severe Sepsis and Septic Shock," *N. Eng. J. Med.* 317:653–658 (1987).

Brennan et al., "A Prospective Randomized Trial of Total Parenteral Nutrition after Major Pancreatic Resection for Malignancy," *Ann. Surg.*, vol. 220 pp. 436–444 (1994).

Buchman et al., "Parenteral Nutrition Leads to a Decrease in Intestinal Mucosal Thickness and an Increase in Intestinal Permeability in Man," *Gastroenterology*, vol. 104, p. A612 (1993).

Deitch et al., "The Gut as a Portal of Entry for Bacteremia," *Ann. Surg.*, vol. 205, p. 681 (1987).

Deitch et al., "Elemental Diet–Induced Immune Suppression Is Caused by Both Bacterial and Dietary Factors," *JPEN*, vol. 17(4), pp. 332–336 (1993).

Deitch, "Bacterial Translocation of the Gut Flora," *J. Trauma*, vol. 30(12), pp. S184–S189 (1990).

Deitch, "Intestinal Permeability Is Increased in Burn Patients Shortly after Injury," *Surgery*, vol. 107, pp. 411–416 (1990).

Flynn, "Bombesin–Like Peptides in the Regulation of Ingestive Behavior," *Ann. N.Y. Acad. Sci.*, vol. 739, pp. 120–134 (1994).

Gawin et al., "Effects of Gastrin–Releasing Peptide and Analogues on Guinea Pig Nasal Mucosal Secretion," *Am. J. Physiol.*, vol. 264, pp. L345–L350 (1993).

Gibbs et al., "The Actions of Bombesin–Like Peptides on Food Intake," *Ann. N.Y. Acad. Sci.*, vol. 547, pp. 210–216 (1998).

Hilderbrand et al., "Human Gastrin–Releasing Peptide: Biological Potency in Humans," *Regulatory Neuropeptides*, vol. 36, pp. 423–433 (1991).

Hinshaw et al., "Effect of High–Dose Glucocorticoid Therapy on Mortality in Patients with Clinical Signs of Systemic Sepsis," *N. Eng. J. Med.*, vol. 317, pp. 659–665 (1987).

Kreger et al., "Gram–Negative Bacteremia IV. Re-evaluation of Clinical Features and Treatment in 612 Patients," *Am. J. Med.*, vol. 68, p. 344 (1980).

Kudsk et al., "Enteral Versus Parenteral Feeding," *Ann. Surg.*, vol. 215(5), pp. 503–513 (1992).

Langkamp–Henken et al., "Increased Intestinal Permeability Following Blunt and Penetrating Trauma," *Crit. Care Med.*, vol. 23(4), pp. 660–664 (1995).

Lee et al., "Role of Neuropeptides in the Regulation of Feeding Behavior: a Review of Cholecystokinin, Bombesin, Neuropeptide Y, and Galanin," *Neurosci. Biobehav. Rev.*, vol. 18, pp. 313–323 (1994).

Li et al., "Effects of Parenteral and Enteral Nutrition on Gut–Associated Lymphoid Tissue," *J. Trauma*, vol. 39(1), pp. 44–52 (1995).

Mahaffey et al., "Parenteral Nutrition in the Swiss Mouse," *Fed. Proceed. Abs.*, vol. 43, p. 848 (1984).

Mestecky, "The Common Mucosal Immune System and Current Strategies for Induction of Immune Responses in External Secretions," *J. Clin. Immunol.*, vol. 7, pp. 265–276 (1987).

Moore et al., "Early Enteral Feeding, Compared with Parenteral, Reduces Postoperative Septic Complications," *Ann. Surg.*, vol. 216, pp. 172–183 (1992).

Moore et al., "Benefits of Immediate Jejunostomy Feeding after Major Abdominal Trauma–a Prospective, Randomized Study," *J. Trauma*, vol. 26, pp. 874–881 (1986).

Moore et al., "TEN Versus TPN following Major Abdominal Trauma–Reduced Septic Morbidity," *J. Trauma*, vol. 29, pp. 916–923 (1989).

Reed et al., "A Simple Method of Estimating Fifty Per Cent Endpoints," *Am. J. Hyg.*, vol. 27, pp. 493–497 (1936).

Renegar et al., "Passive Transfer of Local Immunity to Influenza Virus Infection by IgA Antibody," *J. Immunol.*, vol. 146, pp. 1972–1978 (1991).

Renegar et al., "Immunoglobulin A Mediation of Murine Nasal Anti–Influenza Virus Immunity," *J. Virol.*, vol. 65, pp. 2146–2148 (1991).

Robinson et al., "Effects of Hemorrhage and Resuscitation on Bacterial Antigen–Specific Pulmonary Plasma Cell Function," *Crit. Care Med.*, vol. 19(10), pp. 1285–1293 (1991).

Salmi et al., "Regulation of Lymphocyte Traffic to Mucosa–Associated Lymphatic Tissues," *Gastro. Clin. North Am.*, vol. 20, pp. 495–505 (1991).

Sitren, "Total Parenteral Nutrition in the Mouse: Development of a Technique," *JPEN*, vol. 7, pp. 582–586 (1983).

Spindel, "Mammalian Bombesin–Like Peptides," *Trends Neurosci.*, vol. 9, pp. 130–133 (1986).

Tanaka et al., "Morphological Alteration of Gut–Associated Lymphoid Tissue after Long–Term Total Parenteral Nutrition in Rats," *Cell Tissue Res.*, vol. 266, pp. 29–36 (1991).

Tomasi, "Mechanisms of Immune Regulation at Mucosal Surfaces," *Rev. Infect. Dives.*, vol. 5, pp. S784–S792 (1993).

Van Tol et al., "Neuroenteric Peptides Affect Natural Killer Activity by Intestinal Lamina Propria Mononuclear Cells," *J. Neuroimmunol.*, vol. 42, pp. 139–145 (1993).

Ziegler et al., "Increased Intestinal Permeability Associated with Infection in Burn Patients," *Arch. Surg.*, vol. 123, pp. 1313–1319 (1988).

Ziegler et al., "Treatment of Gram–Negative Bacteremia and Septic Shock with HA–1A Human Monoclonal Antibody against Endotoxin," *N. Eng. J. Med.*, vol. 324, pp. 429–436 (1991).

* cited by examiner

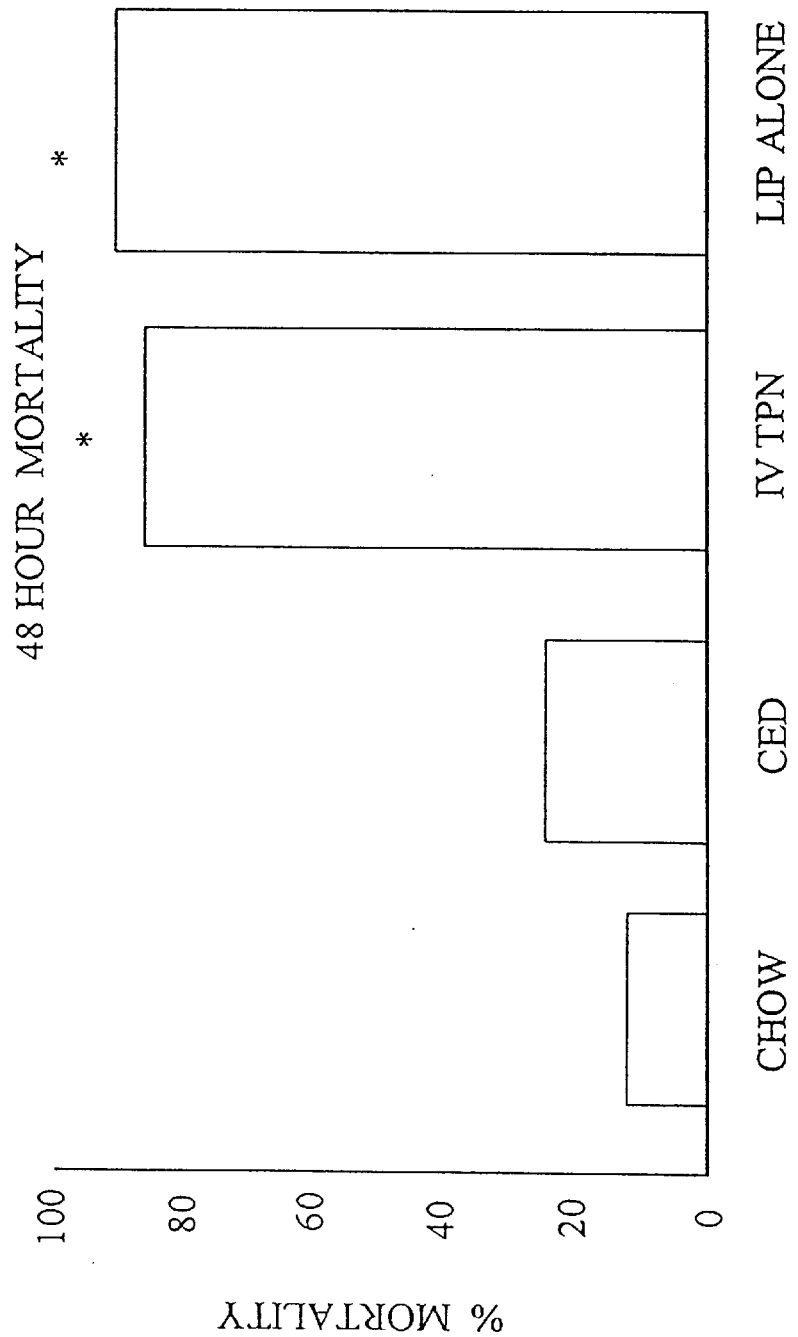

SEQUENCE LISTING

<160> NUMBER OF SEQ ID NOS: 1

<210> SEQ ID NO 1
<211> LENGTH: 7
<212> TYPE: PRT
<213> ORGANISM: Homo sapiens

<400> SEQUENCE: 1

Trp Ala Val Gly His Leu Met
 1               5

REDUCTION OF IMPAIRMENT OF RESPIRATORY TRACT MUCOSAL IMMUNITY

CONTINUING DATA

This application is a continuation-in-part of application Ser. No. 08/842,877, filed Apr. 17, 1997, which is incorporated herein by reference and which claims benefit under 35 U.S.C. §119 of provisional application Ser. No. 60/015,835, filed Apr. 19, 1996 and of provisional application Ser. No. 60/029,689, filed Oct. 31, 1996; all of which are incorporated herein by reference.

BACKGROUND OF THE INVENTION

1. Field of the Invention

The present invention relates to reducing or preventing impairment of respiratory tract mucosal immunity and risk of pneumonia associated with a lack of enteral feeding, such as with the use of total parenteral nutrition (TPN) or, more generally, with a lack of immunological stimulation of the gastrointestinal tract through oral or gastrointestinal feeding. In particular, the present invention relates to methods of reducing or preventing impairment of respiratory tract mucosal immunity. The present invention also relates to compositions useful in such methods.

2. Description of the Related Art

Infectious complications are the most common cause of death following trauma in patients without head injuries (Baker et al., *Am. J. Surg.*, 140:144–150 (1980)), and a frequent cause of morbidity and mortality in malnourished patients, patients sustaining surgical complications, and patients requiring prolonged intensive care unit (ICU) stays. Despite intravenous (IV) nutrition, multiple antibiotics, and aggressive ICU care, mortality from sepsis (i.e., the presence of pathogenic organisms or their toxins in the blood or tissues) averages 30%, with a range of 20–60% depending upon the patient population studied (Bone et al., *Crit. Care Med.*, 17:389–393 (1989); Bone et al., *N. Eng. J. Med.*, 317:653–658 (1987); Ziegler et al., *N. Eng. J. Med.*, 324:429–436 (1991); Hinshaw et al., *N. Eng. J. Med.*, 317:659–665 (1987); and Kreger et al., *Am. J. Med.*, 68:344–34 (1980)). Septic morbidity, especially pneumonia, is significantly reduced in critically injured patients when enteral feeding rather than parenteral feeding or no feeding at all is provided (Kudsk et al., *Ann. Surg.*, 224:531–543 (1996). This suggests that enteral feeding provides benefits to host defenses (Kudsk et al., *Ann. Surg.*, 215:503–513 (1992); Moore et al., *J. Trauma*, 26:874–881 (1986); Moore et al., *J. Trauma*, 29:916–923 (1989); and Moore et al., *Ann. Surg.*, 216:172–183 (1992)).

The mechanisms responsible for improved recovery with the use of enteral feeding are poorly understood, but it is hypothesized that lack of enteral feeding leads to a breakdown in the gastrointestinal barrier, thus allowing molecules and perhaps bacteria to gain entry into the body resulting in inflammation and distant infection (Deitch, *J. Trauma*, 30:S184–S189 (1990); Deitch, *Surgery*, 107:411–416 (1990); Ziegler et al., *Arch. Surg.*, 123:1313–1319 (1988); Deitch et al., *Ann. Surg.*, 205:681 (1987); and Deitch, *Perspect. Crit. Care*, 1:1–31 (1988)). Most investigators have studied barrier integrity by focusing on changes in gut morphology and permeability to bacteria and macromolecules (Bushman et al., *Gastroenterology*, 104:A612 (1993)).

Nutritional models which preserve IgA (i.e., immunoglobulin A) within the mucin layer also appear to preserve normal gastrointestinal (GI) colonization and reduce bacterial translocation (Deitch et al., *JPEN*, 17:332–336 (1993); and Haskel et al., *Ann. Surg.*, 217:634–643 (1993)). Although systemic responses to injury increase gut permeability in some patients, data demonstrating that this increased permeability causes infectious complications, such as pneumonia, are not convincing (Deitch, *Surgery*, 107:411–416 (1990); Ziegler et al., *Arch. Surg.*, 123:1313–1319 (1988); and Langkamp-Henken et al., *Crit. Care Med.*, 23:660–664 (1995)).

Components in mucosal defense and barrier integrity unregulated by bombesin include lactoferrin, peroxidases, lysozymes, the mucin, and high molecular weight glycoprotein. IgA is one of the primary immunologic defenses against many mucosal infections. Moreover, a critical component in mucosal defense and barrier integrity is the availability of secretory IgA (sIgA) in the mucin layer coating the mucosa (Svanborg et al. in Ogra et al., eds., *Handbook of Mucosal Immunology*, 71–78; and Killian et al. in Ogra et al., eds., *Handbook of Mucosal Immunology*, 127–140). sIgA binds or agglutinates bacteria, viruses, and potentially other toxic molecules, eliminating the key to invasive mucosal infection, i.e., adherence of infectious agents to human mucosal cells (Svanborg in Ogra et al., eds., *Handbook of Mucosal Immunology*, 71–78). Levels of IgA are dependent upon adequate numbers of functioning immunocompetent cells in the lamina propria and a cytokine milieu appropriate to the production of IgA (Kiyono et al. in Ogra et al., eds., *Handbook of Mucosal Immunology*, 263–274; and Lebman et al. in Ogra et al., eds., *Handbook of Mucosal Immunology*, 243–250). As IgA is released from plasma cells within the lamina propria, it is transported through mucosal epithelia cells by secretory components. In the mucin layer, sIgA binds and agglutinates potential noxious agents without inducing inflammation. sIgA also appears to improve the functional capabilities of other immune cells such as, neutrophils, to mount defenses against infectious agents.

Once initial activation of precursor IgA-producing cells occurs within the Peyer's patches, the antigen-sensitized cells undergo mitotic changes and the resulting B lymphoblasts migrate to regional lymph nodes and eventually to the systemic circulation via the thoracic duct (Tomasi Jr., *Rev. Infect. Dis.*, 5:S784–S792 (1983)). Experiments using whole bacteria, bacterial products, live or killed viruses, or modified viral antigens have shown that the antigen-sensitized precursor cells home not only to the GI tract but also to the respiratory tract, and mammary, parotid, and lacrimal glands where they produce IgA for transport through the epithelial cells into external secretions if the appropriate T cell signals and antigenic stimulation exist (Kiyono et al. in Ogra et al., eds., *Handbook of Mucosal Immunology*, 263–274; Mestecky et al. in Ogra et al., eds., *Handbook of Mucosal Immunology*, 357–372; Mestecky, J., *J. Clin. Immunol.*, 7:265–276 (1987); and McGhee et al., *Vaccine*, 10:75–88 (1992)).

These observations have led to the concept of a common mucosal immune system and explain the extra-intestinal effects of enteral or parenteral feeding on respiratory tract immunity. The concept of a common mucosal immune system may be the link between intestinal changes and extra-intestinal susceptibility to infection, in particular the respiratory tract.

The human body devotes significant resources to maintain mucosal immunity, including 50% of its functioning immune cells to produce secretory IgA to help control its endogenous microbial GI flora (Brandtzaeg in Ogra et al., eds., *Handbook of Mucosal Immunology*, 3–8; Tomasi in Ogra et al., eds., *Handbook of Mucosal Immunology,* 251–262). The mucosal immune circuit initially begins with antigenic uptake via M cells, which are the cells overlying the intestinal lymphatic follicle of the Peyer's patches (PP). B cells (i.e., B lymphocytes), sensitized by antigen processed within the Peyer's patches, then migrate to the mesenteric lymph nodes where, under the appropriate cytokine milieu, they proliferate and migrate via the thoracic duct into the vascular tree. Once in the vascular system, these sensitized cells home to the lamina propria of the intestine, producing IgA which plays an important role in gut barrier function (Ottaway, *Gastro. Clin. North Am.,* 20:511–529 (1991); and Salmi et al., *Gastroenterol. Clin. North Am,* 20:495–505 (1991)).

Specialized enteral nutritional support has been used to reduce malnutrition and the incidence of infectious complications in critically ill persons. Certain patients, however, are often unable to tolerate enteral feedings and must be fed parenterally. Lack of enteral feeding or a lack of immunological stimulation of the GI tract, such as may occur with intravenous TPN, for example, can lead to atrophy of the small intestinal gut-associated lymphoid tissue (GALT); decreases in intestinal and respiratory tract IgA levels; as well as increases in mucosal permeability, bacterial overgrowth, and bacterial translocation. Lack of enteral feeding or a lack of immunological stimulation of the gastrointestinal tract also impairs established respiratory tract mucosal immunity to an IgA-mediated infectious viral agent and to bacteria which generate specific IgA responses such as *Pseudomonas aeruginosa*. This is consistent with the results of experiments which show that the route and type of nutrition affects levels of IgA, bacterial flora changes, and mucosal permeability. With few exceptions, bacterial overgrowth, mucosal permeability, and increased translocation of both bacteria and macromolecules have shown an inverse correlation with intestinal IgA levels.

Neuropeptides are hormones released by nerve fibers within the intestinal wall. Bombesin (BBS), a tetradecaneuropeptide analogous to mammalian gastrin-releasing peptide, stimulates the release of gastrointestinal hormones, increases levels of intestinal sIgA (Debas et al., *Am. Surg.,* 161:243–249 (1991)), reduces bacterial translocation (Haskel et al., *Ann. Surg.,* 217:634–643 (1993)), and improves mortality in a lethal enterocolitis model (Chu-Ku et al., *Ann. Surg.,* 220:570–577 (1994)). Additionally, bombesin may up-regulate specific cellular immunity, either directly or acting through other hormones released in response to its administration (Jin et al., *Dig. Dis. Sci.,* 34:1708–1712 (1989)).

Bombesin, originally isolated from frog skin, is structurally related to mammalian gastrin-releasing neuropeptide (Spindel, *Trends Neurosci.,* 9:130–133 (1986)). This neuropeptide stimulates gastric and pancreatic secretion, alters gastrointestinal motility, and elicits the release of a variety of gastrointestinal hormones, including gastrin, somatostatin, cholecystokinin, pancreatic polyneuropeptide, insulin, glucagon, and neurotensin (Pascual et al. in Ogra et al., eds., *Handbook of Mucosal Immunology,* 203–216; and Debas et al., *Am. J. Surg.,* 161:243–249 (1991)).

In experiments using IV administration of bombesin to stimulate human natural killer cell activity against human K-562 tumor cells (Van Tol et al., *J. Neuroimmunol.,* 42:139–145 (1993)), in vivo bombesin infusion produced a greater antitumor response than in vitro bombesin incubation, suggesting that mediators other than bombesin may be involved in the increased mobilization of active NK cells into the blood stream. In addition, peripheral blood lymphocytes contain receptors for neurotensin, a neuropeptide released in response to bombesin administration (Evers et al., *Surgery,* 116:134–140 (1994)).

Bombesin has been mainly studied for its satiety effect in humans (Gibbs et al., *Ann. N.Y. Acad. Sci.,* 547:210–216 (1998); Hilderbrand et al., *Regulatory Neuropeptides,* 36:423–433 (1991); Muurahainen et al., *Am. J. Physiol.,* 264:R350–R354 (1993); Flynn, *Ann. N.Y. Acad. Sci.,* 739:120–134 (1994); and Lee et al., *Neurosci. Biobehav. Rev.,* 18:313–323 (1994)). However, binding sites for gastrin-releasing neuropeptide have been documented in human bronchi from specimens obtained from patients undergoing thoracotomy for carcinoma (Baraniuk et al., *Neuropeptides,* 21:81–84 (1992)), and bombesin, as well as other neuropeptides, has been found in the respiratory epithelium of the nasal passages (Hauser-Kronberger et al., *Acta. Otolaryngol.,* 113:387–393 (1993); Gawin et al., *Am. J. Physiol.,* 264:L345–L350 (1993)). Moreover, exogenous administration of bombesin stimulates both in vivo and in vitro human nasal mucus and serous cell secretions, thus increasing total protein, lysozyme, and glycoconjugate secretion, and, thereby, acting as a secretagogue in the upper respiratory tract passages (Baraniuk et al., *Am. J. Physiol.,* 262:L48–L52 (1992)). No increase in albumin secretion accompanies this increased secretion, suggesting that bombesin does not exert its effects through vasodilatation, increases in vascular permeability, or increases in plasma transit across the epithelium.

There is a need in the art for methods and compositions for reducing or preventing impairment of respiratory tract mucosal immunity associated with a lack of enteral feeding, such as total parenteral nutrition (TPN) or fasting. There is also a need in the art for methods and compositions for reducing the rate of respiratory infection by pathogenic microorganisms associated with a lack of enteral feeding or lack of immunological stimulation of the GI tract. Finally, there is a need in the art for methods and compositions for reducing the atrophy or dysfunction of the GALT of an animal associated with a lack of enteral feeding or lack of immunological stimulation of the GI tract. The present invention answers these needs.

SUMMARY OF THE INVENTION

The present invention is directed to methods for reducing the impairment of respiratory tract mucosal immunity and, in particular, upper respiratory tract mucosal immunity, associated with a lack of enteral feeding or a lack of immunological stimulation of the GI tract. Methods of the invention administer a therapeutically effective amount of a neuropeptide selected from the group consisting of bombesin, gastrin-releasing polypeptide, a neuropeptide having an amino acid C terminus corresponding to Trp-Ala-Val-Gly-His-Leu-Met-NH$_2$ [SEQ ID NO:1], or mixtures thereof In addition, the methods of the invention administer a therapeutically effective amount of a compound which stimulates the release of one or more of those neuropeptides. The methods of the invention also administer a therapeutically effective amount of a compound which is released in response to such neuropeptides.

The present invention is also directed to methods of reducing the rate of infection by a pathogenic microorganism in an animal associated with a lack of enteral feeding or a lack of immunological stimulation of the gastrointestinal tract. The methods administer a therapeutically effective amount of a neuropeptide selected from the group consisting of bombesin, gastrin-releasing polypeptide, a neuropeptide having an amino acid C terminus corresponding to Trp-Ala-Val-Gly-His-Leu-Met-NH$_2$ [SEQ ID NO:1], or mixtures thereof. The methods also administer a therapeutically effective amount of a compound which stimulates the release of one or more of those neuropeptides. The methods also administer a therapeutically effective amount of a compound which is released in response to such neuropeptides.

Moreover, the present invention is also directed to methods of reducing the atrophy or dysfunction of the small intestinal gut-associated lymphoid tissue (GALT) and generalized mucosal immunity of an animal associated with a lack of enteral feeding or a lack of immunological stimulation of the gastrointestinal tract. In the embodiment, the methods administer to the animal a therapeutically effective amount of a neuropeptide selected from the group consisting of bombesin, gastrin-releasing polypeptide, a neuropeptide having an amino acid C terminus corresponding to Trp-Ala-Val-Gly-His-Leu-Met-NH$_2$ [SEQ ID NO:1], or mixtures thereof The methods also administer a therapeutically effective amount of a compound which stimulates the release of one or more of those neuropeptides. In addition, the methods administer a compound which is released in response to a neuropeptide, such as those listed above.

In addition, the present invention is directed to compositions useful in reducing impairment of respiratory tract mucosal immunity and, in particular, upper and lower respiratory tract mucosal immunity. Such compositions may contain a therapeutically effective amount of a neuropeptide and, optionally, a pharmaceutically acceptable carrier, wherein the neuropeptide is selected from the group consisting of bombesin, gastrin-releasing polypeptide, a neuropeptide having an amino acid C terminus corresponding to Trp-Ala-Val-Gly-His-Leu-Met-NH$_2$ [SEQ ID NO:1], or mixtures thereof In another embodiment of the invention, the compositions may contain a pharmaceutically acceptable carrier and a therapeutically effective amount of a compound which stimulates the release of such neuropeptides. In still another embodiment of the invention, the compositions may contain a pharmaceutically acceptable carrier and a therapeutically effective amount of a compound which is released in response to a neuropeptide such as bombesin, gastrin-releasing polypeptide, a neuropeptide having an amino acid C terminus corresponding to Trp-Ala-Val-Gly-His-Leu-Met-NH$_2$ [SEQ ID NO:1], or mixtures thereof It is to be understood that both the foregoing general description and the following detailed description are exemplary and explanatory and are intended to provide further explanation of the invention as claimed. Other objects, advantages and novel features will be readily apparent to those skilled in the art from the following detailed description of the invention.

BRIEF DESCRIPTION OF THE FIGURE

The file of this patent contains at least one drawing executed in color. Copies of this patent with color drawing(s) will be provided by the Patent and Trademark Office upon request and payment of the necessary fee.

FIG. 4. 48 Hour Mortality following Pneumonia

DETAILED DESCRIPTION OF THE INVENTION

Figure 1:
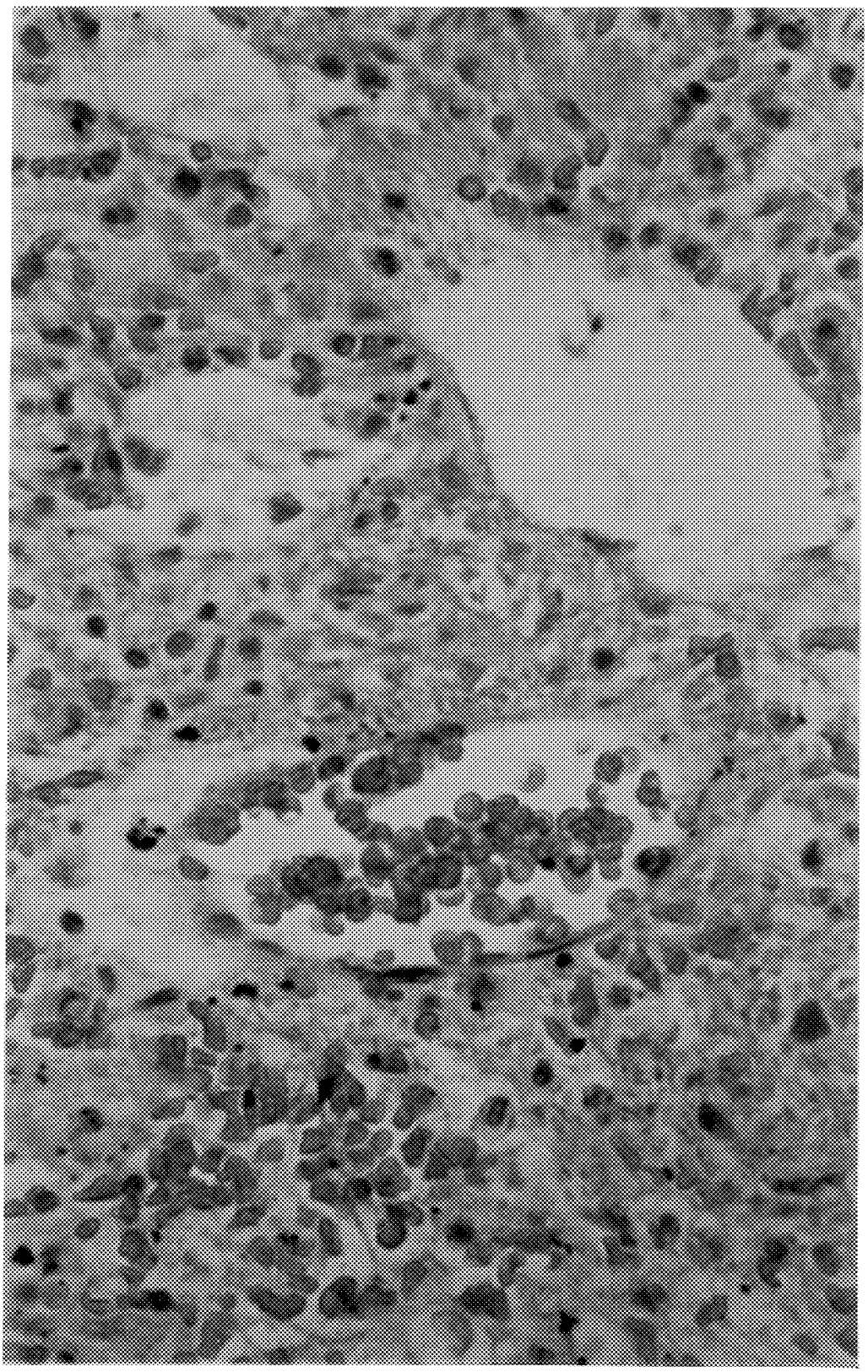
FIG. 1. Histologic Sections Demonstrating Diffuse Pneumonia and Visible Bacteria in LIP only animals following Lethal Pneumonia.

As discussed above, investigators have been actively seeking to define the mechanism of protection altered with lack of enteral feeding such as parenteral nutrition or fasting and to compensate for its loss because of increased infectious complications associated with parenteral nutrition or lack of enteral feeding. Hormonal modulation is one avenue of research. Histologically, the lymphocyte population of the gut mucosa is concentrated in juxtaposition to the entire nerve fibers. Neuroimmune communication is evidenced by lymphoid alterations following release of a variety of neuropeptides.

The present invention, as discussed above, relates to the discovery that IV TPN reduces small intestinal GALT mass; depletes Peyer's patches, intraepithelial, and lamina propria lymphocytes; depresses the T cell CD4$^+$/CD8$^+$ ratio within the intestinal lamina propria; and reduces intestinal IgA levels. Although the precise mechanism behind the clinically significant increases in infectious complications associated with parenteral nutrition has not been completely defined, changes within the GALT and IgA production and other cellular aspects of immunity may well play a significant role in infection of the upper and lower respiratory and GI tracts associated with lack of immunological stimulation of these regions.

Specific cellular and IgA mucosal defense develops after antigen processing and migration of cells to the submucosal spaces (Cebra et al. in Ogra et al., eds., *Handbook of Mucosal Immunology*, 151–158). Secretory IgA, or sIgA, is a primitive defense used to protect moist epithelial surfaces. sIgA is released at the apical surface of epithelial cells to coat the mucosal surface and bind to bacterial adhesions, preventing attachment to the mucosa and allowing clearance via normal luminal transit. sIgA may also support other cellular responses of immunity. Production and secretion of IgA are controlled by the cytokine milieu created by the T- and B-cell populations of the mucosal lamina propria (Tomasi, TB, Ogra et al., eds., *Handbook of Mucosal Immunology*, 3–8). Therefore, TPN-induced down-regulation of the IgA stimulating cytokines, IL-4, IL-S, IL-6 and/or IL-10, may reduce the volume of IgA and cellular responsiveness available for mucosal protection, thereby increasing the risk of bacterial adherence and invasion. Not coincidentally, most nosocomial infections in critically ill intensive care unit (ICU) patients tend to be due to pathogens which elicit a specific IgA response or are capable of producing a IgA protease, reinforcing the concept that IgA is important for mucosal defense.

The GALT appears to be exquisitely sensitive to route and type of nutrition. Small intestine GALT is preserved in animals fed chow or a complex enteral diet, while intravenous TPN produces a generalized atrophy of GALT B and T cells (i.e., B and T lymphocytes) within the lamina propria, Peyer's patches (PP), and intraepithelial spaces. Decreases in intestinal IgA parallel this atrophy. Moreover, the GALT not only provides cells for its own mucosal defense, but it also releases sensitized B and T cells from the Peyer's patches which home to other mucosal sites, providing significant effector immune function to the respiratory tract, mammary glands, salivary gland, and genitourinary tract (Phillips-Quagliata et al. in Orga et al., eds., *Handbook of Mucosal Immunology*, 225–239). IgA produced by these cells plays a role in upper and lower respiratory tract immunity or mucosal defense.

In particular, the present invention relates to the discovery that neuropeptides, such as bombesin and bombesin-like neuropeptides, attenuate TPN-associated depression of B- and T-cell populations within the small intestine, increases intestinal IgA, and prevents depression of the CD4$^+$/CD8$^+$ ratio of the cells within the lamina propria. Since intestinal and extra-intestinal immunity are closely linked via the common mucosal immune system, and neuropeptides, such as bombesin and bombesin-like neuropeptides, attenuate TPN-induced GALT atrophy, exogenous administration of such neuropeptides according to the invention reverses, and preferably prevents, the impairment of respiratory tract mucosal immunity known to occur following IV-TPN in immunized animals to an IgA-mediated infectious viral challenge or to bacteria known to generate a specific IgA response. This is shown by the following examples, which demonstrate that bombesin prevents mucosal immunity impairment and depressed intestinal IgA levels. Bombesin has broader effects, including up-regulation of extra-intestinal mucosal immunity.

As demonstrated in the examples below, TPN reduces the ability of previously immunized mice to adequately defend against an IgA-specific upper respiratory tract viral rechallenge as well as a lower respiratory tract bacterial challenge, and bombesin reverses these detriments. It is plausible that, because of the intimate relationship of the neuroenteric system to the lymphoid system, bombesin acts to maintain adequate cell numbers, up-regulate those cells, and/or stimulate those cells responsible for mucosal immunity and IgA production, consequently enhancing mucosal immunity. Also, these observations further add to the concept of a common mucosal immune system, since these neuropeptides are endogenous to the gastrointestinal tract and also affect the upper and lower respiratory tract.

The invention is directed to methods for reducing, preferably eliminating, impairment of respiratory tract mucosal immunity and, in particular, upper and lower respiratory tract mucosal immunity, associated with a lack of enteral feeding of complex diet(s) (e.g. chow or complex enteral diet (CED)) or lack of immunological stimulation of the gastrointestinal tract in animals. One such method administers a therapeutically effective amount of a neuropeptide selected from the group consisting of bombesin, gastrin-releasing polypeptide, a neuropeptide having an amino acid C terminus corresponding to Trp-Ala-Val-Gly-His-Leu-Met-NH$_2$ [SEQ ID NO:1], or mixtures thereof Another method administers a therapeutically effective amount of a compound which stimulates the release of such neuropeptides. A method of the invention may also administer a therapeutically effective amount of a compound which is released in response to a neuropeptide such as bombesin, gastrin-releasing polypeptide, a neuropeptide having an amino acid C terminus corresponding to Trp-Ala-Val-Gly-His-Leu-Met-NH$_2$ [SEQ ID NO:1], or mixtures of such neuropeptides.

The invention is also directed to methods of reducing the rate of infection, preferably preventing infection, of the respiratory tract and, in particular, the upper and lower respiratory tract, caused by pathogenic microorganisms such as viruses, bacteria, fungi, etc., associated with a lack of enteral feeding of complex diet(s) (e.g. chow or complex enteral diet (CED)) or a lack of immunological stimulation of the GI tract in animals. Risk of infection, such a pneumonia, occurring in the upper and lower respiratory tract may also be reduced or, preferably, prevented by such methods. Methods according to this embodiment of the invention entail administering to an animal a therapeutically effective amount of a neuropeptide such as bombesin, gastrin-releasing polypeptide, a neuropeptide having an amino acid C terminus corresponding to Trp-Ala-Val-Gly-His-Leu-Met-NH$_2$ [SEQ ID NO:1], or mixtures thereof The methods may also involve administering a therapeutically effective amount of a compound which stimulates the release of these same neuropeptides. Also envisioned by this embodiment of the invention are methods administering a therapeutically effective amount of a compound which is released in response to the neuropeptides.

The invention is further directed to methods for reducing the atrophy or dysfunction of the small intestinal gut-associated lymphoid tissue (GALT) of an animal associated with a lack of enteral feeding of complex diet(s) (e.g. chow or CED) or a lack of immunological stimulation of the gastrointestinal tract. The methods administer to the animal a therapeutically effective amount of a neuropeptide a neuropeptide selected from the group consisting of bombesin, gastrin-releasing polypeptide, a neuropeptide having an amino acid C terminus corresponding to Trp-Ala-Val-Gly-His-Leu-Met-NH$_2$ [SEQ ID NO:1], or mixtures thereof The methods may also administer a therapeutically effective amount of a compound which stimulates the release of such neuropeptides. In an alternative embodiment, the methods administer a compound which is released in response to those neuropeptides.

Another embodiment of the invention are compositions useful in reducing impairment of respiratory tract mucosal immunity and, in particular, upper and lower respiratory tract mucosal immunity. The compositions contain a therapeutically effective amount of a neuropeptide and, optionally, a pharmaceutically acceptable carrier. The neuropeptide may be selected from the group consisting of bombesin, gastrin-releasing polypeptide, a neuropeptide having an amino acid C terminus corresponding to Trp-Ala-Val-Gly-His-Leu-Met-NH$_2$ [SEQ ID NO:1], or mixtures thereof. Alternatively, the compositions may contain a therapeutically effective amount of a compound which stimulates the release of such neuropeptides and, optionally, a pharmaceutically acceptable carrier. The invention also relates to compositions containing a therapeutically effective amount of a compound released in response to a neuropeptide and, optionally, a pharmaceutically acceptable carrier.

The compositions of the present invention may also comprise one or more pharmaceutically acceptable carriers, other adjuvants, and active substances. Exemplary pharmaceutical carriers and adjuvants are described in U.S. Pat. No. 5,397,803, which is specifically incorporated by reference.

For both the methods and compositions of the invention, a therapeutically effective amount is defined as an amount which reduces or prevents the impairment of GI and/or upper and lower respiratory tract mucosal immunity. According to the present invention, a therapeutically effective amount of neuropeptide or other compound according to the invention (i.e. a compound which stimulates the release of neuropeptide or a compound released in response to a neuropeptide) may preferably vary from about 15 ng/kg to about 100 ng/kg, with administration rates of about 3 to about 4 times per day. Preferably, the amount of the neuropeptide or other compound administered daily may range from about 0.1 g/kg body weight to about 3.0 g/kg body weight.

As discussed above, the methods and compositions according to the present invention comprise administering neuropeptides, such as bombesin, a neuropeptide having similar function or activity as bombesin (a "bombesin-like neuropeptide"), a compound released in response to either bombesin or a bombesin-like neuropeptide, a compound which stimulates the release of bombesin or a bombesin-like neuropeptide, or mixtures thereof.

A preferred neuropeptide employed in the present invention is bombesin, which has a 7-amino acid C terminus, Trp-Ala-Val-Gly-His-Leu-Met-NH$_2$ [SEQ ID NO:1]. Other bombesin-like neuropeptides having an analogous 7-amino acid C terminus which may be used, include, but are not limited to, gastrin-releasing polypeptide.

Compounds which are released in response to a neuropeptide selected from the group consisting of bombesin, gastrin-leasing polypeptide, a neuropeptide having an amino acid C terminus corresponding to Trp-Ala-Val-Gly-His-Leu-Met-NH$_2$ [SEQ ID NO:1], or a mixture thereof, include, but are not limited to, gastrin, somatostatin, cholecystokinin, pancreatic polypeptide, insulin, glucagon, neurotensin, and substance P.

Compounds which stimulate the release of bombesin or bombesin-like neuropeptides include neurostimulants.

Neuropeptides, compounds which stimulate the release of neuropeptide or compounds released in response to a neuropeptide of the methods and compositions of the invention as described above may be administered by means known in the art. Suitable modes of administration include, but are not limited to, enteral, intravenous, or parenteral administration. Preferably, the neuropeptides and compounds of the methods and compositions of the invention are administered as a supplement to a patient's TPN if TPN is used. Examples of parenteral routes of administration include, but are not limited to, subcutaneous, intramuscular, respiratory, or IV injection, as well as nasopharyngeal, mucosal, and transdermal absorption. The neuropeptides and compounds of the methods and compositions of the invention can also be administered via the gastrointestinal tract in a protected form, such as where the protected form is a liposome.

The following examples are given to illustrate the present invention. It should be understood, however, that the invention is not to be limited to the specific conditions or details described in these examples.

EXAMPLE 1

This example demonstrates that specialized nutrition exhibits a significant influence on an IgA-mediated defense against infection. In particular, it is shown that IV feeding of a TPN solution impairs the ability of immune mice to respond with an IgA-mediated antiviral defense, and that the route of nutrition influences both intestinal and extra-intestinal mucosal immunity.

MATERIALS AND METHODS

Animals

The studies prepared herein conform to the guidelines for the care and use of laboratory animals established by the Animal Care and Use Committee of The University of Tennessee, and protocols were approved by that committee. Male ICR mice Harlan, Indianapolis, Ind.) were housed in an American Association for Accreditation of Laboratory Animal Care accredited conventional facility under controlled conditions of temperature and humidity with a 12:12 hour light:dark cycle. Mice were quarantined and fed commercial mouse chow (RMH 3200 Agway, Syracuse, N.Y.) with water ad libitum for 2 weeks prior to protocol entry. During the experiments, the mice were housed in metal metabolism cages with wire-grid bottoms to eliminate coprophagis and bedding ingestion.

Virus Preparation

A/PR8-Mt. Sinai (H1N1) influenza virus was the gift of Dr. Parker A. Small, Jr., (University of Florida, Gainesville). To generate a pool, virus was grown in eggs, pooled, filtered through a 0.45 micron filter, aliquoted, and stored at −70° C. A 50% lethal dose for mice (LD$_{50}$) was established by the total respiratory tract inoculation of 50 µl of 10-fold serial dilutions of the virus pool intranasally into anesthetized mice, generating a fatal pneumonia. The virus pool contained 10$^5$ LD$_{50}$ per ml.

Experimental Protocol

Mice were inoculated with 20 µl of a 1:10 dilution of the virus pool stock of A/PR8 (H1N1), a mouse-adapted influenza virus, intranasally (IN) while awake. This route assures infection without producing pneumonia and produces sound systemic and mucosal immunity in convalescent mice three weeks post-inoculation (Renegar et al., *J. Virol.*, 65:2146–2148 (1991)).

Three weeks after inoculation, animals were randomized to receive chow with an intravenous catheter (n=10), IV TPN (n=10), or a complex enteral diet of NUTREN® (n=11) via gastrostomy. In animals randomized to gastrostomy, a sham neck incision was performed, and animals with IV lines had a sham laparotomy. Under general anesthesia (Ketamine 100 mg/kg and Acepromazine Maleate 10 mg/kg mixture), a silicone rubber catheter (0.012" I.D.×0.025" O.D. Baxter, Chicago, Ill.) was inserted into the vena cava through the right jugular vein or directly into the stomach. Twenty microliters of blood were drawn and the plasma stored at 4° C. prior to ELISA to document the presence of virus-specific serum IgG. Lines were tunneled subcutaneously from either the right jugular vein or the gastrostomy site and exited the tail at its midpoint. Animals were partially immobilized by tail restraint during infusion; this model does not produce physical or chemical evidence of stress (Sitren et al., *JPEN*, 7:582–586 (1983)).

Catheterized animals were immediately infused with saline at a rate of 4 ml per day with an increase in rate to a goal of 10 ml/day in the chow and IV TPN groups and 15 ml/day in the NUTREN® group. For the first two days animals were allowed ad libitum access to chow. On the third day following surgery, animals received only the assigned nutrition. The TPN solution contained 4.1% amino acids and 34.3% glucose (1538 kcal/L), in addition to electrolytes and vitamins. The nonprotein calorie/nitrogen ratio of the TPN solution was 158:1 kcal/g nitrogen. NUTREN® (Clintec, Chicago, Ill.) contained 12.7% carbohydrate, 38% fat, and 4% protein (1000 kcal/L) in addition to electrolytes and vitamins. The nonprotein calorie/nitrogen ratio of NUTREN® was 156:1 kcal/g N. These feedings provided ~15kcal energy and 95 mg N, meeting the calculated requirements for mice weighing 25 to 30 g.[26] (Li, J; Kudsk, K. A.; Gocinski, B. et al. *J Trauma* 1995; 39(1):44–52).

After five days of their respective diets, animals were given IN challenge twice successively during a 20-minute period with 10 µl of the influenza virus (20 µl total) while awake. Diets were maintained after the challenge until sacrifice. At 40 hours, the animals were sacrificed by exsanguination under anesthesia. The trachea was clamped at the thoracic inlet through a midline neck incision, and 600µl cold Dulbecco's Modified Eagle Media (DMEM) supplemented with 10% fetal calf serum (FCS) and antibiotics, as detailed below, were infused into the proximal trachea. The wash fluid draining from the nostrils was collected in a microcentrifuge tube, placed on ice, and immediately processed for virus. The small intestine was excised from the ligament of Treitz to the ileocecal valve and rinsed three times with total 15 ml chilled Hanks' balanced salt solution ASS), and the intestinal contents collected in plastic tubes in an ice bath. The length of the small intestinal segments was recorded under a standardized vertical extension with a 2-gram weight and the contents stored in −70° C. freezer for further IgA analysis. The Peyer's patches were also harvested for cell populations.

Antibody Quantitation

IgA was measured in intestinal washings in a sandwich enzyme-linked immunosorbent assay (ELISA), using a polyclonal goat anti-mouse IgA (Sigma, St. Louis, Mo.) to coat the plate, a purified mouse IgA (Sigma, St. Louis, Mo.) as standard, and a horseradish peroxidase conjugated goat anti-mouse IgA.

Serum influenza-specific IgG was determined by ELISA assay as described previously (Mestecky, *J. Clin. Immunol.*, 7:265–276 (1987)). Affinity-purified goat anti-mouse IgG and alkaline phosphatase-linked rabbit anti-goat antibodies were obtained from Sigma (St. Louis, Mo.).

Cell Isolations

Lymphocyte isolations from the PP were performed as previously described (Li et al., *J. Trauma*, 39:44–52 (1995)). The PP were excised from the serosal side of the intestine and teased apart with 18-gauge needles. The fragments were treated with Type 1 collagenase (Sigma, St. Louis, Mo.) (50 U/ml) in minimal essential medium (MEM) for 60 minutes at 37° C. with constant rocking. After collagenase digestion, the cell suspensions were passed through nylon filters.

Flow Cytometry

To determine the phenotypes of the lymphocytes isolated from the PP, $10^5$ cells were suspended in 50 $\mu$l HBSS containing either fluorescein-conjugated (FITC-) anti-CD3 (clone 145-2C11, Pharmigen, San Diego, Calif.) or phycoerythrin-conjugated (PE-) goat anti-mouse immunoglobulin (Souther Biotechnology Associates, Birmingham, AL) to identify T cells and B cells, respectively, or in FITC-anti-CD4 (clone RM4-5) and PE-anti-CD8 (clone 53–67, Pharmigen, San Diego, Calif.) to identify the two T-cell subsets. All antibodies were diluted to 2.5 $\mu$l/ml in HBSS containing 1% BSA and 0.1% azide; incubations were for 30 minutes on ice. Following staining, the cells were washed twice in HBSS/0.25% BSA and were fixed in 1% paraformaldehyde (Sigma, St. Louis, Mo.). Flow cytometry analysis was performed on a Profile I (Coulter Co., Hileah, Ill.).

Viral Assays

Viral samples were serially diluted (10 fold) in DMEM supplemented with 2.5 $\mu$g/ml amphotericin B, 50 $\mu$g/ml gentamicin, and 10% FCS. Triplicate 100 l of a $2\times10^5$ cells/ml suspension of MDCK cells in antibiotic-supplemented DMEM-10% FCS was added. Plates were incubated at 5% $CO_2$ and 37° C. Culture fluid was removed 24 hours later and replaced with DMEM containing 2.5 $\mu$g/ml gentamicin, 2.5 jig/ml amphotericin B, 2 $\mu$g/ml trypsin. Plates were incubated 4 days longer. Viral growth was determined by a hemagglutination assay. To each well, 50 $\mu$l of a 0.5% suspension of chicken red blood cells was added. Hemagglutination was read after 1–2 hours in the cold, and viral titers were calculated by the method of Reed and Muench (Reed et al., *Am. J. Hyg.*, 27:493–497 (1936)).

Statistical Analysis

All data were expressed as the mean ± the standard error of the mean. Statistical analysis was carried out by analysis of variance and Scheffe's multiple comparison and simple linear regression procedure, using Statview (Brain Power, Inc., Calabasas, Calif.) software. The Fisher exact test was used for analysis of virus shedding.

Viral Model

The infection chosen was an A/PR8 (H1N1) mouse-adapted influenza virus documented to be IgA-mediated (Renegar et al., *J. Virol.*, 65:2146–2148 (1991); and Renegar et al., *J. Immunol.*, 146:1972–1978 (1991)). Following inoculation of non-immune mice, the virus proliferates within the mucosal epithelial cells and can be cultured from the respiratory tract for 7 to 10 days until normal immune mechanisms clear the virus. When convalescent (immune) mice are challenged, virus is cleared in less than 24 hours.

In immune animals, serum virus-specific IgG confirms systemic immunity, but experiments designed to test passive immunity or block mucosal immunoglobulins show that respiratory tract mucosal immunity is IgA mediated. The intravenous administration of influenza-specific polymeric IgA induces temporary passive immunity against the virus in nonimmune mice as IgA is transported from the serum into the nasal secretions Renegar et al., *J. Immunol.*, 146:1972–1978 (1991)). Convalescent (immune) mice challenged with virus administered with anti-IgG and anti-IgM antibodies maintain immunity and efficiently clear the virus; administration of anti-IgA antiserum with the challenge eliminates immunity Venegar et al., *J. Virol.*, 65:2146–2148 (1991)).

A viral rather than a bacterial challenge was used in the present examples to test established IgA responses for several reasons. First, it assured that animals did not have prior immunologic 'experience' with the infectious challenge. Second, the assay techniques are exquisitely sensitive to specific antiviral antibody. Third, the model appears to be purely IgA mediated. A similar underlying mechanism for both anti-influenza immunity and immunity to bacterial pathogens causing pneumonia is likely since many pathogenic infecting organisms in intensive care units, such as *Haemophilus influence, Steptococcus pneumoniae, Proteus mirabilis, Proteus vulgaris, Serritia marcescens, Escherichia coli, Klebsiella pneumoniae*, Acinetobater, *Candida albicans, Candida tropicalis,* and *Torulopsis glabrata,* have been shown to generate a specific IgA response (Killian et al. in Ogra et al., eds., *Handbook of Mucosal Immunology,* 127–140). These bacterial organisms account for a large number of the nosocomial pneumonias occurring in an intensive care setting. Normally, these organisms are kept in check by microflora balance which is disrupted by antibiotic administration and other aspects of standard medical care, and by IgA defenses potentially influenced by mechanisms implicit in our animal model. Susceptibility to induced pseudomonas pneumonia increases with hemorrhagic shock in a time frame characterized by depressed respiratory IgA levels (Robinson et al., *Crit. Care Med.,* 19:1285–1293 (1991)).

RESULTS

All animals fed via the GI tract maintained normal immunity against the mouse-adapted virus. Despite confirmed immunity at the time of randomization to diet by the presence of antiviral IgG within the serum, 50% of IV-fed animals lost their immune defense allowing viral proliferation in the respiratory tract. Atrophy in IV-TIN-fed animals was confirmed by the changes in the Peyer's patches in the current study. This suggests that IV-TPN both produces atrophy within the GALT and impairs respiratory tract immunity to an IgA mediated viral challenge.

There were no significant differences in body weight at the beginning or end of the experiment although animals randomized to chow had significantly greater weight gain during the experiment than IV TPN animals. There were no significant differences between the animals receiving TPN or a complex enteral diet of NUTREN®), as shown below in Table 1.

In addition, there was a significant decrease in total cell yield within the Peyer's patches from animals receiving the TPN IV ($p<0.05$) compared with the chow ($p<0.05$) or a complex enteral diet of NUTREN®) ($p<0.50$) animals, as shown below in Table 2. There were significant decreases in CD4 and CD8 cells in the TPN group as compared with chow ($p<0.05$), and a complex enteral diet of NUTREN®) ($p<0.05$). Overall, there were no significant differences in the $CD4^+/CD8^+$ ratio between groups.

The IV TPN mice had significantly fewer B cells than the chow or the complex enteral diet of NUTREN®) animals ($p<0.05$). Intestinal IgA was significantly lower in the TPN group ($p<0.05$) than chow or complex enteral diet of NUTREN®) groups, as shown below in Table 3.

All animals had positive serum anti-viral IgG titers at the time of cannulation, documenting systemic immunity. Despite this, after five days of feeding, S out of 10 IV-TPN animals had positive flu virus ($p<0.0001$) culture from nasal washes while all other groups had successfully cleared the viral challenge, as shown below in Table 4.

These results show that basic cellular aspects of mucosal immunity are effected by nutritional manipulation and that IV-TPN impairs IgA-mediated mucosal immunity to A/PR8 mouse-adapted influenza virus in the intact murine upper respiratory tract.

TABLE 1

Animal Body Weight and Weight Gain

| Group | n | Body Weight (g) | Weight Gain (g) |
|---|---|---|---|
| CHOW | 10 | 31.60 ± 1.35 | 2.80 ± 1.23 |
| IV-TPN | 10 | 28.80 ± 1.28 | 0.09 ± 0.91* |
| NUTREN® | 11 | 28.52 ± 1.22 | 0.40 ± 0.79 |

*vs. CHOW, $p < 0.05$

TABLE 2

PP Cell Yield And Subtype (×10⁶)

| Group | Total | B | T | CD4 | CD8 | CD4/CD8 |
|---|---|---|---|---|---|---|
| CHOW | 5.09 ± 0.40 | 3.05 ± 0.28 | 1.40 ± 0.15 | 1.09 ± 0.11 | 0.40 ± 0.05 | 3.04 ± 0.41 |
| IV-TPN | 3.11 ± 0.37*# | 1.86 ± 0.25*# | 0.86 ± 0.09*# | 0.70 ± 0.07*# | 0.22 ± 0.03*# | 3.41 ± 0.37 |
| NUTREN | 4.97 ± 0.40 | 3.03 ± 0.28 | 1.37 ± 0.10 | 1.06 ± 0.09 | 0.40 ± 0.04 | 3.15 ± 0.43 |

*vs. CHOW, $p < 0.05$;
vs NUTREN®, $p < 0.05$

TABLE 3

Intestinal IgA Level

| Group | Intestinal IgA(ug) |
|---|---|
| CHOW | 84.7 ± 8.1 |
| IV-TPN | 52.1 ± 3.3*† |
| NUTREN® | 80.5 ± 6.8 |

*vs. CHOW, $p < 0.05$;
†vs. NUTREN, $p < 0.05$;

TABLE 4

Viral Shedding

| Group | Virus Positive |
|---|---|
| CHOW | 0/10* |
| IV-TPN | 5/10 |
| NUTREN® | 0/11* |

*vs IV-TPN, $p < 0.001$

EXAMPLE 2

The purpose of this example is to demonstrate that IV-TPN is associated with decreases in small intestinal (SI) GALT T cells, B cells, and IgA, and that it reduces the level of IgA within the respiratory tract (RT). The impaired respiratory tract defenses are speculated to be due, at least in part, to reduced respiratory tract IgA levels.

MATERIALS AND METHODS

Materials and methods were the same as those given in Example 1, above.

To determine the time course for these reductions in GALT and document any changes in respiratory tract IgA, 35 mice were sacrificed after receiving IV catheters and 2 days of chow followed by 0 (n=6), 1 (n=6), 2 (n=6), 3 (n=6), 4 (n=6), or 5 days (n=5) of IV-TPN.

Small intestinal and respiratory tract washes were collected and analyzed by ELISA for IgA. Lymphocytes were isolated from Peyer's patches (PP), intraepithelial (IE) spaces, and the lamina propria (LP) and analyzed by flow cytometry. The total cell yield was counted under light microscopy. The results are summarized in Table 5.

RESULTS

TABLE 5

Cell Yield Counts

| | TPN Day 0 | TPN Day 1 | TPN Day 2 | TPN Day 3 | TPN Day 4 | TPN Day 5 |
|---|---|---|---|---|---|---|
| PP Cell | | | | | | |
| T | 2.8 ± .12 | 2.1 ± .32 | 1.6† ± .44 | 0.8† ± .09 | 0.8† ± .12 | 0.8† ± .13 |
| B | 4.8 ± .20 | 3.8 ± .65 | 2.7† ± .67 | 1.3† ± .18 | 1.5† ± .23 | 1.3† ± .21 |
| LP Cell | | | | | | |
| T | 2.4 ± .16 | 2.0 ± .30 | 1.3† ± .16 | 1.2† ± .14 | 1.0† ± .10 | 1.1† ± .23 |
| B | 1.1 ± .10 | 1.0 ± .19 | 0.5† ± .07 | 0.6† ± .10 | 0.4† ± .05 | 0.5† ± .11 |
| $CD4^+/CD8^+$ | 1.9 ± .08 | 1.9 ± .22 | 1.6 ± .21 | 1.6 ± .16 | 1.2† ± .08 | 1.2† ± .05 |
| SI IgA µg | 286.5 ± 107.8 | 221.7 ± 53.5 | 138.6 ± 76.8 | 71.7* ± 25.3 | 47.4† ± 10.4 | 19.3† ± 5.2 |
| RT IgA ng | 267.4 ± 47.8 | 242.5 ± 70.8 | 139.3 ± 35.8 | 129.6* ± 30.1 | 131.8* ± 50.2 | 107.9* ± 17.8 |

Mean ± SE
Compared with Day 0: *$p < .05$, †$p < .01$

The results show that IV-TPN decreases GALT T and B cell numbers in the lamina propria and Peyer's patches by Day 2. The normal lamina propria $CD4^+/CD8^+$ ratio of approximately 2:1 is significantly reduced by Day 4. Decreases in small intestinal and respiratory tract IgA levels accompany decreases in GALT cell numbers, reaching significance by Day 3.

15

CONCLUSION

IV-TPN produces rapid changes in GALT cell profiles and reduces respiratory tract IgA levels consistent with the impairment of respiratory and intestinal IgA-mediated defenses.

EXAMPLE 3

The purpose of this example is to demonstrate, in a model of established respiratory immunity against *Pseudomonas aeruginosa* (Ps) pneumonia, complete preservation of respiratory immunity with chow or a complex enteral diet(s) (CED) and complete loss of protection with IV TPN. Route and type of nutrition influence respiratory tract immunity.

MATERIALS AND METHODS

Except as otherwise provided here, the materials and methods were the same as those given in Example 1.

Liposome Preparation

Bacterial polysaccharide (PS) containing liposomes were prepared by the detergent dialysis technique as described by Abraham et al., *Vaccine*, 10:461–468 (1992). Briefly, 8 µM of cholesterol, phosphatidylserine, and phosphatidylcholine (Sigma) were combined and dried under $N_2$ and the resulting film lyophilized for up to 24 hours. Ten mg purified alkali-labile *Pseudomonas aeruginosa* A lipopolysaccharide (the gift of Dr. Gerald Pier, Channing Laboratory, Harvard University, Boston, Mass.) was dissolved in 500 µl HEPES buffer (150 mM NaCl, 10 mM HEPES, 1 mM EDTA, ph 7.4), added to the lipid film, and emulsified by vigorous pipetting. The emulsion was incubated for 30 minutes at 4° C., then 240 µl 1M octylglucoside (Sigma, St. Louis, Mo.) was added and the mixture shaken vigorously. The sample was placed in Spectra/Por dialysis tubing (m.w. cutoff 3500, from Spectrum Medical Industries, Inc., Los Angeles, Calif.) and dialyzed against 100 ml of HEPES buffer containing 2.4 g SM-2 Bio-Beads (Bio-Rad Laboratories, Hercules, Calif.). After 24 hours, the liposome preparation was placed on an A5M column (Bio-Gel A-5m, Bio-Rad Laboratories, Hercules, Calif.) and the liposome fraction (in the void volume) collected. Polysaccharide (PS) incorporation ranged from 30–70%. Calculation of immunization dose was based upon the original lipid concentration (15 mg) since this produced consistent immunity.

Bacteria

PA was plated on trypticase soy agar (TSA) with 5% SRBCs 48 hours before animals were inoculated. The plated PA was serially diluted and suspended to A595 nm of 0.670±0.010 after 24 hours. Triplicate samples were obtained and assayed for bacterial count by overnight incubation on TSA. The suspension was stored overnight at 4° C. On the morning of inoculation, bacterial counts were obtained. The bacterial suspension was centrifuged at 3500 rpm for 30 minutes at 4° C., the supernatant discarded, the pellet resuspended in 7 ml of sterile PBS, and the centrifugation repeated. Bacteria were centrifuged a total of three times to decrease the chances of contamination with free bacterial endotoxin. The pellet was resuspended to a final concentration of $3.0 \times 10^9$ bacteria per ml or $1.2 \times 10^8$ bacteria per 40 µl.

Immunization

Each mouse was immunized intranasally (IN) with liposomes containing 160 µg lipid and 30–70 jig polysaccharide or with liposomes (160 µg lipid) alone. Calculation of the liposome dose for immunization was based on the amount of lipid present. Mice were gently restrained by hand and 100 µl of a PBS suspension of either Ps-containing liposomes or control non-Ps-containing liposomes placed on the nares. The mouse was allowed to inhale the inoculum. Successful inoculation was evidenced by a change in breathing pattern and brief cyanosis. Ten days later, the mice were randomized to treatment groups and underwent surgery for the placement of intravenous catheters.

Statistical Analysis

Statistical analysis was performed using a Two-Tailed Fischer's Exact test.

Histology

The lungs and trachea of 3 LIP alone, 3 chow, 4 CED, and 4 IV-TPN mice were removed following death or sacrifice and fixed for two weeks in neutral buffered 10% formalin. The fixed tissues were embedded in paraffin and cut to a thickness of 5 microns. Sections were stained with hematoxylin and eosin B and read by a board-certified veterinary pathologist blinded to the study group.

Histological studies were performed to confirm pneumonia. Lung sections from 14 out of 15 immunized mice showed acute suppurative pneumonia with alveolitis and bronchiolitis. All nonimmunized controls showed necrotizing fibrinous pneumonia and marked pulmonary edema. Bacteria were seen in all cases of pneumonia but were more numerous in the control LIP-alone group. Representative sections are pictured in FIG. 1.

FIG. 1 shows Histologic Sections Demonstrating Difuse Pneumonia and Visible Bacteria in LIP only animals following Lethal Pneumonia.

Experimental Protocol

*Pseudomonas aeruginosa* was administered intratracheally to determine mortality at increasing doses, and liposomes containing Ps antigens (LIPAg) were used to generate effective respiratory immunization. In the final experiment, mice received LIPAg to establish immunity and then were randomized to chow, CED, or IV-TPN. After 5 days of diet, mice received live intratracheal Ps and mortality recorded at 24 and 48 hours.

Experiment 3a

Development of Pneumonia Model

Mice were anesthetized via subcutaneous injection of a ketamine hydrochloride (100 mg/kg of body weight) and acepromazine maleate (10 mg/kg of body weight) mixture then vertically suspended by their upper incisors with a strip of silicone tubing pinned to styrofoam board. Traction was applied to the tongue using small forceps and 40 µl of a bacteria/PBS suspension were subsequently administered by the intratracheal route with a blunt tipped 21G needle. Nine groups of nonimmune chow fed mice were each challenged with live bacteria using this technique, with each group receiving increasing doses of bacteria ranging from $1.0 \times 10^7$ to $1.6 \times 10^8$ bacteria. Each group was placed in a separate shoe box container and received ad libitum chow (RMH 3200 Agway, Syracuse, N.Y.) and water. Mortality was observed at 24 hours and 48 hours. Four additional groups of animals underwent the above procedure with each group receiving increasing doses of bacteria ranging from $8.0 \times 10^7$ to $9.5 \times 10^7$ bacteria. Mortality was observed at 24 and 48 hours.

Each group was given increasing doses of bacteria to determine mortality rates. A substantial increase in mortality was noted between animals receiving $8.0 \times 10^7$ bacteria and $1.0 \times 10^8$ bacteria (Table 6). Subsequently, 4 separate groups of mice were given increasing doses of bacteria from $8.0 \times 10^7$ bacteria to $1.0 \times 10^8$ bacteria. The LD50 was approximately $9.0 \times 10^7$ bacteria. A protocol dosage of $1.2 \times 10^8$ bacteria was used because it assured high mortality in nonimmune (LIP alone) chow-fed animals.

TABLE 6

Pseudomonas LD50-Naive Animals

| Bacterial Count | Mortality |
| --- | --- |
| $1.0 \times 10^7$ | 0/5 |
| $2.0 \times 10^7$ | 0/5 |
| $4.0 \times 10^7$ | 0/5 |
| $6.0 \times 10^7$ | 1/10 |
| $8.0 \times 10^7$ | 0/11 |
| $10.0 \times 10^7$ | 10/11 |
| $12.0 \times 10^7$ | 5/5 |
|  | LD100 |
| $14.0 \times 10^7$ | 5/5 |
| $16.0 \times 10^7$ | 5/5 |
| $8.0 \times 10^7$ | 1/4 |
| $8.5 \times 10^7$ | 1/4 |
| $9.0 \times 10^7$ | 3/5 |
|  | LD50 |
| $9.5 \times 10^7$ | 3/4 |

Experiment 3b

Immunization Model

Unanesthetized mice received 100 μl PS-containing liposomes (n=17) or 100 μl of control non-PS liposomes (n=15) IN as previously described. After 10 days, all mice were anesthetized and administered 40 μl of PBS containing $1.2 \times 10^8$ live bacteria intratracheally as described above. Each group was placed in a separate shoe box container and received ad libitum chow (RMH 3200 Agway, Syracuse, N.Y.) and water. Mortality was observed at 24 hours and 48 hours.

At 24 hours, nonimmune chow-fed animals suffered a 47% mortality compared with no mortality in the immune chow-fed animals (p<0.002). Mortality at 48 hours was slightly higher in both groups, reaching 67% in the nonimmune animals versus 12% in the immune mice (p<0.003) (Table 7).

TABLE 7

Liposome Alone vs. Liposome with Pseudomonas Antigen Mortality

|  | Liposome Alone | Liposome with Antigen |  |
| --- | --- | --- | --- |
| 24 hours | 7/15 (47%) | 0/17 (0%) | p < 0.005 |
| 48 hours | 10/15 (67%) | 2/17 (12%) | p < 0.005 |

The LD50 and LD100 were $9.0 \times 10^7$ and $12.0 \times 10^7$, respectively. Immunization reduced mortality from 66% to 12%.

Experiment 3c

Nutritional Manipulation of Respiratory Immunity

Sixty-four mice were immunized IN with Ps-containing liposomes, and 20 mice received non-Ps-containing liposomes (LIP alone) (FIG. 1). After 10 days, immunized mice were randomized to receive IV TPN (n=24), chow (n=20), or CED (n=20). Mice randomized to the IV TPN and chow groups received internal jugular catheters under ketamine/acepromazine anesthesia. Through a right internal jugular approach, a silicone rubber catheter (0.3 mm I.D. and 0.6 mm O.D., Baxter, Chicago, Ill.) was inserted into the vena cava. The proximal end of the catheter was tunnelled subcutaneously over the spine and exited the tail at its midpoint. The mice were placed into metal metabolism cages and partially immobilized by tail restraint to protect the catheter during infusion. This technique is an acceptable method of nutritional support that does not induce physical or biochemical stress (Sitren et al., *J Parenter Enteral Nutr.*, 7:582–586 (1983)). Mice randomized to the CED groups received gastrostomy tubes. Through a vertical midline incision, the stomach was delivered into the wound. A 7-0 silk pursestring suture was placed on the posterior wall of the stomach followed by a gastrotomy within the center of the pursestring suture using a 25G needle. The silicone catheter was inserted into the gastrotomy. Omentum was mobilized and fee tied around the insertion of the gastrostomy tube using a 7-0 silk suture. The proximal end of the catheter was tunnelled subcutaneously over the spine and exited the tail at its midpoint. All mice receiving venous catheters underwent sham laparotomies while those receiving gastrostomy tubes underwent sham neck incisions.

Figure 2:
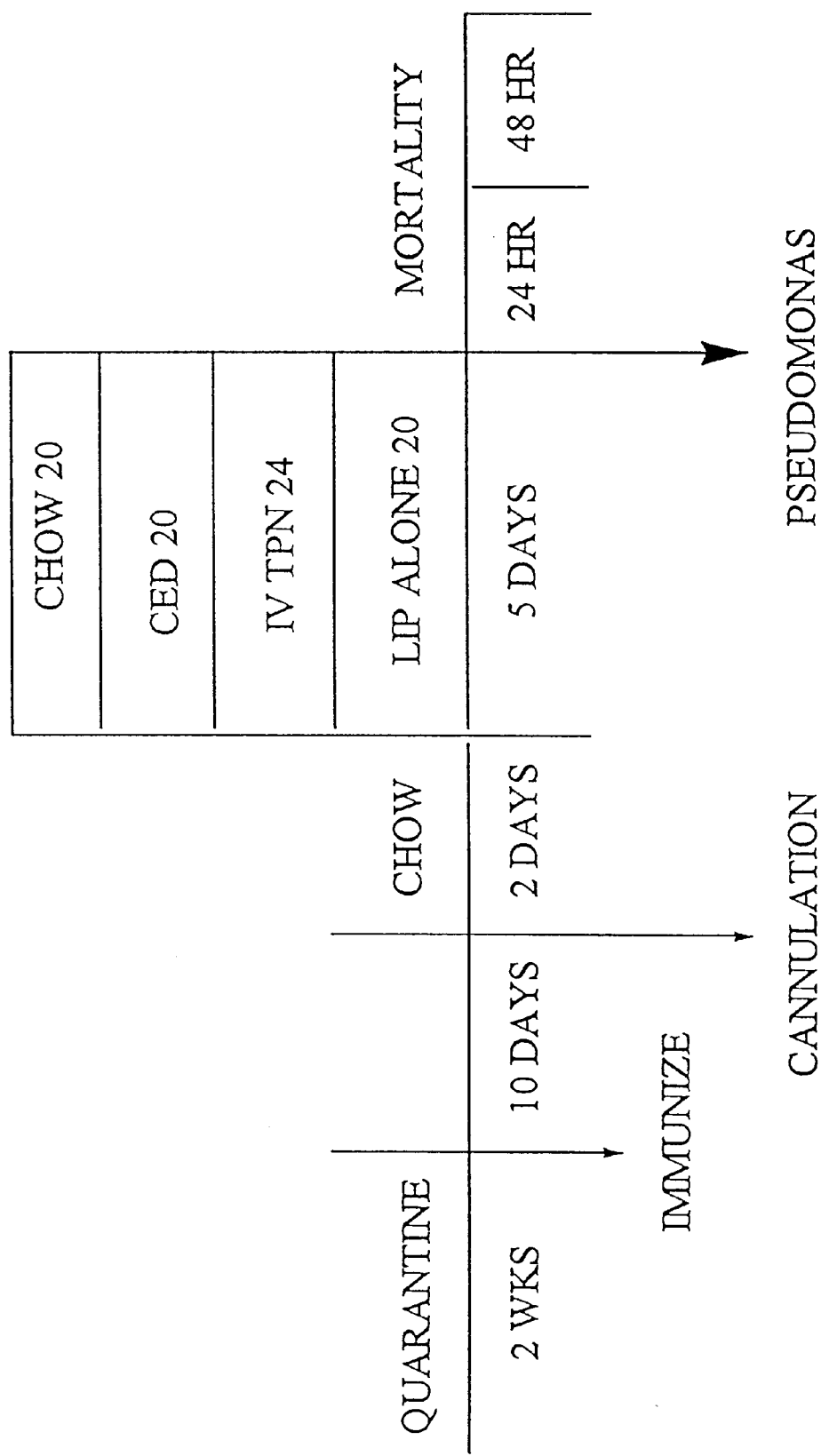
FIG. 2. Bacterial Pneumonia Protocol.

Catheterized mice were immediately connected to an infusion pump (Instech Laboratories, Plymouth Meeting, Pa.), and received 0.9% saline at 4 mL/day for 48 hours with ad libitum access to chow and water (FIG. 2). On postoperative day 2, mice received their respective feeds. Chow fed animals received 4 ml of 0.9% saline IV along with ad libitum chow and water throughout the study. The TPN fed animals initially received 4 ml/day of TPN and were advanced to a goal rate of 10 μl per day by the third day of feeding. The TPN solution contained 4.1% amino acids, 34.3% glucose, electrolytes, and multivitamins with a nonprotein calorie to nitrogen ratio of 663.6 kJ/g nitrogen. The CED (NUTREN®, Clintec, Chicago, Ill.) fed animals initially received 4 ml per day were advanced to a goal rate of 15 ml per day by the third day of feeding. NUTREN® contained 12.7% carbohydrate, 3.8% fat, and 4.0% protein (4200 kJ/L) along with electrolytes and vitamins providing a nonprotein calorie to nitrogen ratio of 665.2 kJ/g nitrogen. These feedings met the calculated nutritional requirements of mice weighing between 25–30 g (*Nutrient Requirements of Laboratory Animals*, Washington, D.C.: National Academy of Science; 43:848–853 (1978). Mice given intranasal liposomes without the antigen served as unmolested controls and did not undergo surgery. They received ad libitum chow and water throughout the study.

After receiving their respective diets for 5 days, all mice were anesthetized and challenged with 40 μl of PBS containing $1.2 \times 10^8$ live bacteria intratracheally as described above. Each group was placed in separate shoe box container and received ad libitum chow (RMH 3200 Agway, Syracuse, N.Y.) and water. Mortality was observed at 24 hours and 48 hours. The expired mice were removed at each observation period and the lungs were harvested and placed in formaldehyde for pathological analysis. Surviving animals were humanely sacrificed on day 3 and lungs harvested for pathology.

Figure 3:
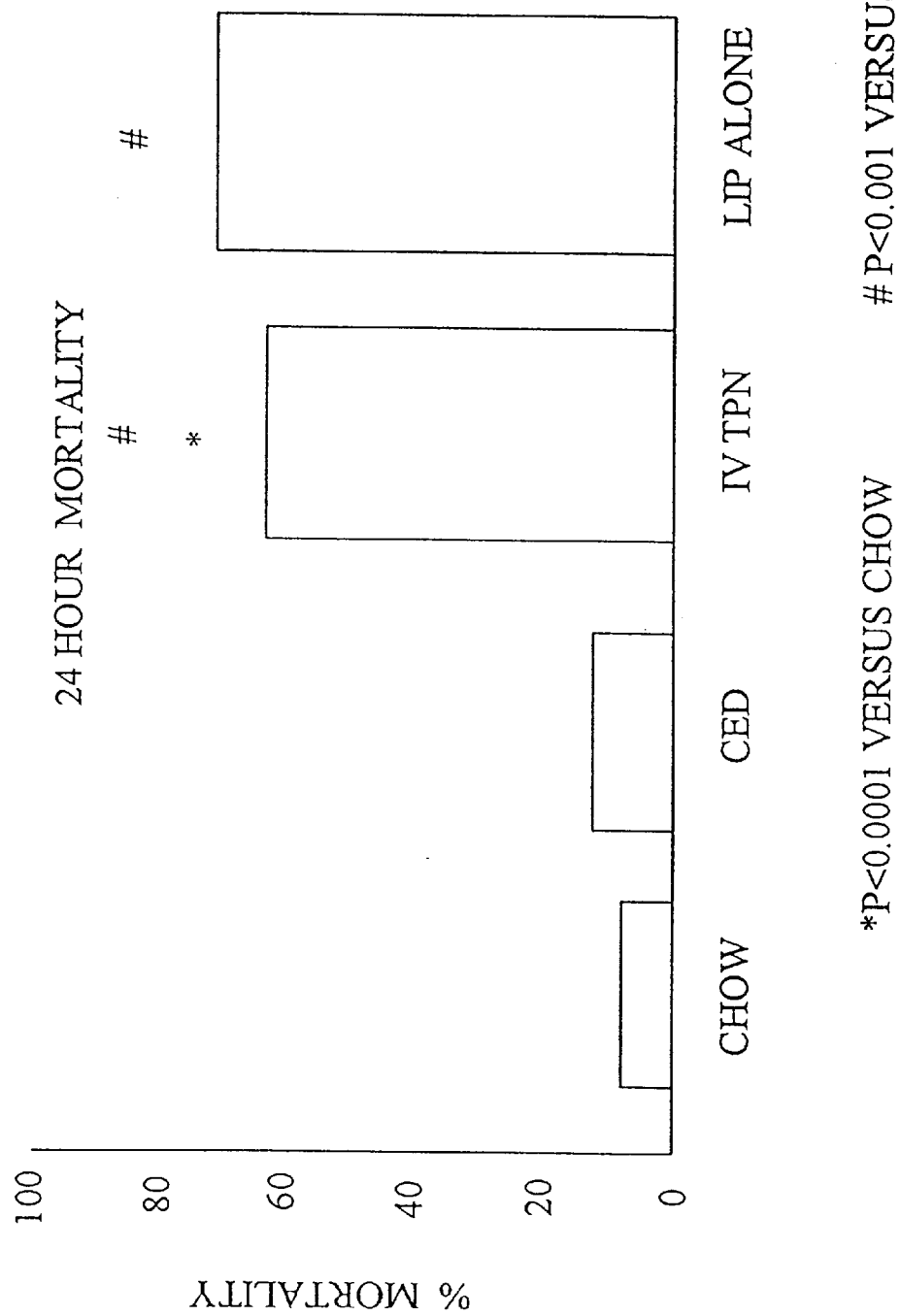
FIG. 3. 24 Hour Mortality following Pneumonia.

At 24 hours, nonimmune chow-fed mice (LIP-alone) had a significantly higher mortality than immune chow-fed (14/20 versus 1/20, p<0.0001) or CED-fed (14/20 versus 2/20, p<0.001) mice (FIG. 3). IV TPN significantly increased mortality compared with chow (I15/24 vs 1/20, p<0.0001) or CED (15/24 vs 2/20, p<0.001). Animals receiving IV TPN had a mortality rate comparable to LIP-alone animals.

At 48 hours, mortality was significantly higher in the nonimmune LIP-alone mice compared with chow (18/20 vs 2/20, p<0.0001) and CED groups (18/20 vs 5/20, p<0.0001) (FIG. 4). Chow or CED mice had a significantly lower mortality than IV T?N mice (2/20 vs 21/24 and 5/20 vs 21/24, respectively, p<0.0001). IV TPN mortality was comparable to the LIP only group (21/24 vs 18/20).

CONCLUSION

Immunization was completely maintained in mice fed chow or a CED and completely lost in animals receiving IV TPN.

Protection against bacterial pneumonia can be induced by prior antigenic immunization. This protection is lost with IV TPN, but completely preserved with chow or complex enteral diets. Both route and type of nutrition influence antibacterial respiratory tract immunity.

EXAMPLE 4

The purpose of this example is to demonstrate the bombesin prevents TPN-induced GALT atrophy, depressed gastrointestinal (GI) and respiratory tract (RT) IgA levels, and impaired nasal antiviral IgA-mediated mucosal immunity.

MATERIALS AND METHODS

Except as otherwise provided here, the materials and methods were the same as those given in Example 1.

After jugular line placement, 41 male ICR mice were randomized to chow (n--8) or IV-TPN (n=33). After 5 days of IV-TPN, the mice received 0 (n=8), I (n-8), 2 (n=10), or 3 days (n=7) of I 5 µg/kg BBS IV tid. The mice were then sacrificed to harvest lymphocytes from Peyer's patches (PP), intraepithelial (IE) and lamina propia (LP) for cell yields. The GI and RT IgA levels were analyzed by ELISA. The results are summarized in Table 8.

TABLE 8

| | Cell Yield Counts | | | | |
|---|---|---|---|---|---|
| | | | TPN-BBS | | |
| | Chow | TPN | Day 1 | Day 2 | Day 3 |
| PP × $10^6$ | 8.0 ± 2.7 | 4.4 ± 1.9* | 5.6 ± 2.1* | 5.8 ± 2.4* | 7.6 ± 2.3† |
| IE × $10^5$ | 6.1 ± 2.1 | 3.6 ± 1.1* | 4.2 ± 1.2* | 5.0 ± 1.2† | 6.1 ± 0.9† |
| LP × $10^6$ | 6.9 ± 2.5 | 4.1 ± 1.9* | 4.2 ± 2.2* | 5.1 ± 1.3† | 6.2 ± 1.4† |
| GI IgA µg | 108 ± 55 | 42 ± 23* | 50 ± 24 | 80 ± 107 | 111 ± 55† |
| RT IgA ng | 600 ± 338 | 284 ± 42* | 215 ± 26* | 356 ± 56* | 528 ± 88† |

*p < 0.05 vs chow, †p < 0.05 vs TPN

EXAMPLE 5

The purpose of this example is to demonstrate that supplementing IV-TPN with subcutaneous injections of bombesin reverses TPN-induced impairment in anti-viral IgA-mediated defenses.

MATERIALS AND METHODS

Animals

The studies reported herein conform to the guidelines for the care and use of laboratory animals established by the Animal Use and Care Committee of the University of Tennessee, and protocols were approved by that committee, as described above in Example 1. The source of the mice is the same as given above in Example 1, and the animals were housed and fed as given above in Example 1.

Experimental Design and Formulas

All mice were administered A/PR8-Mt. Sinai (H1N1) virus, a mouse-adapted influenza strain received as a gift from Dr. Parker A. Small, Jr. (University of Florida, Gainesville). Virus was grown as in Example 1.

Study mice were inoculated intranasally while awake with 20 µL of a 1:10 dilution of stock pooled virus. Following a three week period of convalescence, the mice underwent placement of catheters for IV infusion after intraperitoneal injection of Ketamine (100 mg/kg/body weight) and Acepromazine Maleate (10 mg/kg/body weight) mixture. A silicone rubber catheter (0.012" I.D.¥0.025" O.D. Baxter, Chicago, EL) was inserted into the vena cava through the right jugular vein. The distal end of the catheter was tunneled subcutaneously and exited the tail at its midpoint. The mice were partially immobilized by tail restraint to protect the catheter during infusion. This technique of infusion in the mouse has proven to be an acceptable method of nutrition support and does not produce physical or biochemical evidence of stress.

Catheterized mice were immediately connected to an infusion apparatus and saline infused at an initial rate of 4 ml/d. For the first two days, animals were allowed ad libitum access to chow and then were randomized to one of three experimental diets. The Chow group (Chow, n=12) served as the control group and received an infusion of physiologic saline in addition to standard laboratory mouse diet and water ad libitum. The TPN group (TPN, n-12) received a standard TPN solution (prepared in the hospital pharmacy) intravenously (Li et al., J. Trauma, 39:44–52 (1995)). The TPN solution provided 1538 kcal/L with a nonprotein calorie/nitrogen ratio of 158:1. The bombesin group (BBS, n=12) received an identical TPN solution, as well as bombesin, given by slow IV infusion through their venous catheters, every eight hours at a does of 15 mcg/kg body weight. During postoperative chow feeding, the infusion rates of saline via the respective catheters were increased over a 48-hour period to 10 mild and were continued at those rates for the five days of experimental diet feeding. These feedings provided approximately 15 kcal energy and 95 mg N, meeting the calculated requirements for mice weighing 25–30 g. (Nutrient Requirements of Laboratory Animals. National Research Council Publication No. 10, National Academy of Science, 1978). The mice were allowed two days of chow during post-surgical recovery and then received five days of experimental infusion. After feeding for 5 days, mice were re-challenged with IN virus and continued feeding for another 40 hours. The animals then anesthetized with the Ketamine/Acepromazine Maleate mixture and weighed. The thoracic and abdominal cavities were opened aseptically and the animals exsanguinated by cardiac puncture.

Viral shedding from the URT was determined by collection of nasal secretions; normal convalescent mice shed no virus due to intact IgA-medicated mechanisms. The trachea was clamped at the thoracic inlet through a midline neck incision. A solution of 600 µl of cold Dulbecco's Modified Eagle Media (DMEM) supplemental with 10% fetal calf serum (FCS) and antibiotics, as detailed below, was infused slowly into the tracheal lumen cephalad to the obstruction. The wash fluid draining from the nostrils was collected in a microcentrifuge tube and viral assays were conducted immediately.

Viral samples were serially diluted (10 fold) in DMEM supplemented with 2.5 µg/ml amphotericin B, 50 µg/ml gentamicin, and 10% FCS. Triplicate 100 µl samples of each dilution were placed in 96-well round bottom tissue culture plates. To each well, 100 µl of a 2¥$10^5$ cells/ml suspension of Madin-Darby Canine Kidney (MDCK) cells (American Type Culture Collection (ATCC), Rockville, Md.) in supplemental DMEM-10% FCS were added. Plates were incubated at 5% $CO_2$ and 37°. Culture fluid was removed 24 hours later and replaced with DMEM containing 25% µg/ml amphotericin, and 2 µg/ml trypsin. Plates were incubated 4 days longer. Assay for viral growth was determined by hemagglutination. To each well, 50 µl of a 0.5% suspension of chicken red blood cells were added. Hemagglutination was read after 1–2 hours in the cold.

All data are expressed as the mean ± the standard error of the mean. Data was analyzed using Fisher's exact test and Student's t-test. A p value of 0.05 or less was considered significant.

RESULTS

Body Weight

The pre-experiment weights of all groups were similar. There were no differences in body weight or weight gain between the TPN and bombesin groups, however, both were significant lower than the CHOW group, as shown below in Table 9.

Viral Shedding

Following 6 days of their respective feeding, no mice in the chow group (0/12) shed virus. However, 50% of the mice in the T?N group has positive viral shedding (6/12). Of the mice in the bombesin group, only one was positive for viral shedding (1/12), as shown below in Table 10. The TPN group showed significantly increased viral shedding compared to both the CHOW group and the bombesin group. Bombesin reversed the TPN-associated impairment of URT immunity.

TABLE 9

| | | Animal Body Weight | |
|---|---|---|---|
| Group | n | Pre-Experiment (g) | Post-Experiment (g) |
| CHOW | 12 | 31.6 ± 2.3 | 32.6 ± 2.5 |
| TPN | 12 | 30.6 ± 1.5 | 29.9 ± 2.3 |
| Bombesin | 12 | 29.8 ± 3.1 | 28.0 ± 3.8 |

TABLE 10

| | Viral Shedding | |
|---|---|---|
| Group | Viral Shedding (+) | Positive % |
| CHOW | 0/12 | 0% |
| TPN | 6/12 | 50%*♦ |
| Bombesin | 1/12 | 8.3% |

*p < 0.05 vs Bombesin
♦p < 0.01 vs CHOW

CONCLUSION

The GI tract is an important immune organ functioning not only to control its own resident microbial flora, but also providing a significant effector immune function to other mucosal sites including lung, breast, salivary glands, genitourinary tract, and liver (Salmi et al., *Gastroenterol. Clin. North Am.*, 20:495–505 (1991)). Parenteral nutrition, as well as elemental diets, has a detrimental effect on mucosal immunity. Previous research has shown that TPN reduces small intestinal mass; depletes Peyer's patch, intraepithelial, and lamina propia lymphocytes; depresses the $CD4^+/CD8^+$ ratio within the lamina propia; reduces intestinal sIgA production (Li et al., *J. Trauma*, 39: 44–52 (1995)); increases bacterial translocation (Alverdy et al., *Surgery*, 104:185–190 (1988)); and increases susceptibility to septic challenge. All of these observations relate to break downs in the prevention of bacterial infections and failure of mucosal immunity.

Bombesin was found to prevent the TPN-associated impairment of intestinal and upper respiratory tract mucosal immunity. These examples (4 and 5) also show that hormonal modulation of immunity via supplemental neuropeptides reverses the impairment in IgA-mediated respiratory tract defenses.

EXAMPLE 6

The purpose of this example is to demonstrate bombesin's (BBS's) ability to preserve TPN-suppressed respiratory immunity in a lethal model of Pseudomonas (Ps.) Aeruginosa pneumonia.

MATERIALS AND METHODS 55 mice underwent intranasal inoculation with liposomes (LIP) alone (no immunization) or LIP-containing Ps. antigen (PS). After 10 days, PS mice were catheterized and randomized to chow (n=15), IV-TPN (n=14), or IV-TPN with 15 µg/k tid BBS (n=14). Diets began on the third postoperative day. LIP mice received chow but no catheter. After 5 days of diet, all mice were given an $LD_{100}$ dose of live intratracheal Ps ($1.2 \times 10^8$ bacteria) with mortality noted at 24 and 48 hours. The results are summarized in Table 11.

TABLE 11

| Mortality (number of expired animals/total number of animals) | | | | |
|---|---|---|---|---|
| | | PS Mice | | LIP Mice |
| Mortality | Chow | IV-TPN | BBS-IV-TPN | Chow (no catheter) |
| 24 Hours | 1/15 | 11/14* | 2/14 | 10/12* |
| 48 Hours | 3/15 | 12/14* | 3/14 | 11/12* |

*p < 0.001 vs chow or BBS

Ps. immunization reduces mortality in a gram-negative pneumonia model. Ps. immunization reduced mortality from 92% (LIP) to 20% (chow), but IV-TPN increased mortality (86%) to that of unimmunized animals. BBS prevents this increased mortality. BBS maintains respiratory immunity in Ps. immune IV-TPN mice.

It will be apparent to those skilled in the art that various modifications and variations can be made in the methods and compositions of the present invention without departing from the spirit or scope of the invention. Thus, it is intended that the present invention cover the modifications and variations of this invention provided they come within the scope of the appended claims and their equivalents.

The claimed invention is:

1. A method of reducing the rate of infection of the respiratory tract by a pathogenic microorganism in an animal associated with a lack of enteral feeding or a lack of immunological stimulation of the gastrointestinal tract comprising administering a therapeutically effective amount of a neuropeptide selected from the group consisting of bombesin, gastrin-releasing polypeptide, a neuropeptide having an amino acid C terminus corresponding to Trp-Ala-Val-Gly-His-Leu-Met-NH$_2$, [SEQ ID NO:1], and a mixture thereof.

2. The method of claim 1, wherein the neuropeptide is administered intravenously, parenterally, enterally, or via the gastrointestinal tract in a protected form.

3. The method of claim 2, wherein the animal is undergoing total parental nutrition and the neuropeptide is administered as a part of the animal's total parental nutrition.

4. The method of claim 1, wherein the therapeutically effective amount is about 15 ng/kg to about 100 ng/kg administered about 3 to about 4 times per day.

5. The method of claim 1, wherein the pathogenic microorganism is selected from the group consisting of a virus, a bacterium, and a fungus.

6. A method of reducing the rate of infection of the respiratory tract by a pathogenic microorganism in an animal associated with a lack of enteral feeding or a lack of immunological stimulation of the gastrointestinal tract comprising administering a therapeutically effective amount of a compound which stimulates the release of a neuropeptide selected from the group consisting of bombesin, gastrin-releasing polypeptide, a neuropeptide having an amino acid C terminus corresponding to Trp-Ala-Val-Gly-His-Leu-Met-NH$_2$ [SEQ ID NO:1], and a mixture thereof.

7. A method of reducing the rate of infection of the respiratory tract by pathogenic microorganisms in an animal associated with a lack of enteral feeding or a lack of immunological stimulation of the gastrointestinal tract comprising administering a therapeutically effective amount of a compound which is released in response to a neuropeptide selected from the group consisting of bombesin, gastrin-releasing polypeptide, a neuropeptide having an amino acid C terminus corresponding to Trp-Ala-Val-Gly-His-Leu-Met-NH$_2$, and a mixture thereof.

8. The method of claim 7, wherein the compound is selected from the group consisting of gastrin, somatostatin, cholecystokinin, pancreatic polypeptide, insulin, glucagon, neurotensin, and substance P.

9. The method of claim 7, wherein the compound is administered intravenously, parenterally, enterally, or via the gastrointestinal tract in a protected form.

10. The method of claim 9, wherein the animal is undergoing total parental nutrition and the compound is administered as a part of the animal's total parental nutrition.

11. The method of claim 7, wherein the therapeutically effective amount is about 15 ng/kg to about 100 ng/kg administered about 3 to about 4 times per day.

12. The method of claim 7, wherein the pathogenic microorganism is selected from the group consisting of a virus, a bacterium, and a fungus.

13. A method of reducing the rate of infection of the respiratory tract by a pathogenic microorganism in an animal associated with a lack of enteral feeding or a lack of immunological stimulation of the gastrointestinal tract comprising administering a therapeutically effective amount of a neuropeptide consisting essentially of Trp-Ala-Val-Gly-His-Leu-Met-NH$_2$ [SEQ ID NO:1].

14. The method of claim 13, wherein the neuropeptide is administered intravenously, parenterally, enterally, or via the gastrointestinal tract in a protected form.

15. The method of claim 14, wherein the animal is undergoing total parental nutrition and the neuropeptide is administered as a part of the animal's total parental nutrition.

16. The method of claim 13, wherein the therapeutically effective amount is about 15 ng/kg to about 100 ng/kg administered about 3 to about 4 times per day.

17. The method of claim 13, wherein the pathogenic microorganism is selected from the group consisting of a virus, a bacterium, and a fungus.

18. A composition useful in reducing the rate of infection of the respiratory tract by a pathogenic microorganism in an animal associated with a lack of enteral feeding or a lack of immunological stimulation of the gastrointestinal tract comprising a therapeutically effective amount of a neuropeptide consisting essentially of Trp-Ala-Val-Gly-His-Leu-Met-NH$_2$, [SEQ ID NO:1] and a pharmaceutically acceptable carrier.

* * * * *